US010195150B2

(12) United States Patent
Djordjevic et al.

(10) Patent No.: US 10,195,150 B2
(45) Date of Patent: Feb. 5, 2019

(54) ORALLY DISINTEGRATING TABLET FORMULATION FOR ENHANCED BIOAVAILABILITY

(71) Applicant: Kashiv Pharma, LLC, Bridgewater, NJ (US)

(72) Inventors: Jelena Djordjevic, Basking Ridge, NJ (US); Murali Mohan Bommana, Plainsboro, NJ (US); Wantanee Phuapradit, Montville, NJ (US); Navnit H. Shah, Clifton, NJ (US); Christopher A. Pizzo, Ridgewood, NJ (US)

(73) Assignee: Kashiv Pharma, LLC, Bridgewater, NJ (US)

( * ) Notice: Subject to any disclaimer, the term of this patent is extended or adjusted under 35 U.S.C. 154(b) by 96 days.

(21) Appl. No.: 14/653,071

(22) PCT Filed: Dec. 19, 2013

(86) PCT No.: PCT/US2013/076578
§ 371 (c)(1),
(2) Date: Jun. 17, 2015

(87) PCT Pub. No.: WO2014/100418
PCT Pub. Date: Jun. 26, 2014

(65) Prior Publication Data
US 2016/0120809 A1 May 5, 2016

Related U.S. Application Data

(60) Provisional application No. 61/749,040, filed on Jan. 4, 2013, provisional application No. 61/739,813, filed on Dec. 20, 2012.

(51) Int. Cl.
| | | |
|---|---|---|
| *A61K 9/00* | (2006.01) | |
| *A61K 9/14* | (2006.01) | |
| *A61K 31/57* | (2006.01) | |
| *A61K 31/381* | (2006.01) | |
| *A61K 31/496* | (2006.01) | |
| *A61K 31/4045* | (2006.01) | |
| *A61K 31/4985* | (2006.01) | |
| *A61K 9/20* | (2006.01) | |

(52) U.S. Cl.
CPC .......... *A61K 9/2027* (2013.01); *A61K 9/0056* (2013.01); *A61K 9/146* (2013.01); *A61K 9/2054* (2013.01); *A61K 31/4045* (2013.01); *A61K 31/496* (2013.01); *A61K 31/4985* (2013.01); *A61K 31/57* (2013.01)

(58) Field of Classification Search
CPC ...... A61K 9/0056; A61K 31/57; A61K 9/146; A61K 9/145
See application file for complete search history.

(56) References Cited

U.S. PATENT DOCUMENTS

| | | | |
|---|---|---|---|
| 4,758,598 A | 7/1988 | Gregory | |
| 5,763,476 A | 6/1998 | Delbressine et al. | |
| 6,319,926 B1* | 11/2001 | Cotrel | C07D 487/04 514/249 |
| 6,350,786 B1 | 2/2002 | Albano et al. | |
| 2002/0009494 A1* | 1/2002 | Curatolo | A61K 9/146 424/489 |
| 2002/0034542 A1* | 3/2002 | Thombre | A61K 9/0056 424/465 |
| 2003/0224043 A1 | 12/2003 | Appel et al. | |

FOREIGN PATENT DOCUMENTS

| | | | | |
|---|---|---|---|---|
| CN | 1251312 A | 4/2000 | | |
| EP | 0338404 A1 * | 10/1989 | ............. | A61K 31/57 |

OTHER PUBLICATIONS

Chang, R.K., et al. "Polymethacrylates" in Handbook of Pharmaceutical Excipients. Pharmaceutical Press and American Pharmacists Association 2009 (6th Edition) 525-533.*
"Tolcapone." Merck Index Online 2013. https://www.rsc.org/Merck-Index/monograph/print/m10938/tolcapone?q=authorize (accessed Dec. 21, 2016).*
CAS Registry No. 595-33-5 (Nov. 16, 1984).*
Yeh, Shing-Shing, et al. "Improvement in Quality-of-Life Measures and Stimulation of Weight Gain After Treatment with Megestrol Acetate Oral Suspension in Geriatric Cachexia: Results of a Double-Blind, Placebo-Controlled Study." Journal of the American Geriatrics Society 48.5 (2000): 485-492.*
Gasparini, M., et al. "Cognitive improvement during Tolcapone treatment in Parkinson's disease." Journal of neural transmission 104.8-9 (1997): 887-894.*
Potulska, Anna, et al. "Swallowing disorders in Parkinson's disease." Parkinsonism & related disorders 9.6 (2003): 349-353.*
Badgujar, Bhatu P., and Atish S. Mundada. "The technologies used for developing orally disintegrating tablets: a review." Acta pharmaceutica 61.2 (2011): 117-139.*
Douroumis, Dennis. "Orally disintegrating dosage forms and taste-masking technologies; 2010." Expert opinion on drug delivery 8.5 (2011): 665-675.*
Sheth, Nita, and Wilma C. Diner. "Swallowing problems in the elderly." Dysphagia 2.4 (1988): 209-215.*
Chen, Po-Hung, et al. "Prevalence of perceived dysphagia and quality-of-life impairment in a geriatric population." Dysphagia 24.1 (2009): 1-6.*
Bharawaj, Sudhir, et al. "Orally Disintegrating Tablets: A Review." Drug Invention Today 2.1 (2010).*

(Continued)

*Primary Examiner* — Kevin S Orwig
*Assistant Examiner* — Peter Anthopolos
(74) *Attorney, Agent, or Firm* — Lerner, David, Littenberg, Krumholz & Mentlik, LLP

(57) ABSTRACT

In some aspects of the present invention is a formulation comprising a solid dispersion or intimate mixture of a poorly water soluble drug and an ionic polymer surprisingly exhibiting fast disintegration of tablet.

9 Claims, 5 Drawing Sheets

(56) References Cited

OTHER PUBLICATIONS

Maltoni, M., et al. "High-dose progestins for the treatment of cancer anorexia-cachexia syndrome: a systematic review of randomised clinical trials." Annals of Oncology 12.3 (2001): 289-300.*
Agarwal, V., et al. "Drug delivery: Fast-dissolve systems." Encyclopedia of pharmaceutical technology (2007): 1104-1114.*
Chen, R., et al. "Hypromellose Acetate Succinate" in Handbook of Pharmaceutical Excipients. Pharmaceutical Press and American Pharmacists Association 2009 (6th Edition) 330-332).*
Lunesta® (eszopiclone) Tablets: USFDA Prescribing Information. Sepracor® Inc. (Jan. 2008).*
D. Volpe, "Application of Method Suitability for Drug Permeability Classification," The AAPS Journal, vol. 12(4), pp. 670-678, Dec. 2010.
International Search Report for Application No. PCT/US2013/076578 dated Jul. 4, 2014.
Partial International Search Report for Application No. PCT/US2013/076578 dated Apr. 2, 2014.

* cited by examiner

ORALLY DISINTEGRATING TABLET FORMULATION FOR ENHANCED BIOAVAILABILITY

CROSS-REFERENCE TO RELATED APPLICATIONS

The present application is a national phase entry under 35 U.S.C. § 371 of International Application No. PCT/US2013/076578, filed Dec. 19, 2013, published in English, which claims priority from U.S. Provisional Application No. 61/739,813, filed on Dec. 20, 2012, and U.S. Provisional Application No. 61/749,040, filed on Jan. 4, 2013, all of which are incorporated herein by reference.

BACKGROUND

This disclosure generally relates to formulations containing active pharmaceutical ingredients that have low solubility in water. In aspects, the formulations are solid oral dosage forms. Embodiments of formulations include orally disintegrating tablets.

Many therapeutically useful drug substances have low aqueous solubility and/or low intestinal permeability. These properties complicate the design of dosage forms for delivering the drug substances. The Biopharmaceutics Classification System ("BCS") has been developed to describe drug substances by their solubility and permeability properties:

Class I—high permeability, high solubility drugs that are well absorbed.

Class II—high permeability, low solubility drugs having bioavailability that is limited by the solubilization rate.

Class III—low permeability, high solubility drugs having bioavailability that is limited by the permeation rate.

Class IV—low permeability, low solubility drugs having poor bioavailability and high variability of pharmacokinetics parameters (e.g., AUC and $C_{max}$).

A drug is considered to be highly soluble under the BCS when its highest unit dosage strength is soluble in 250 mL or less of aqueous media over the pH range of 1 to 7.5. Many drug substances, however, fall within Classes II and IV. Formulating dosage forms to deliver such drugs, particularly when larger amounts of the drugs must be delivered in each dose, is very challenging. The absolute drug solubility is not always the most important parameter, since residence times in various sites within the gastrointestinal system after oral administration vary, and it is usually necessary to have a drug in solution during its transit through the particular sites where it can be systemically absorbed. Examples of drugs having low solubility are those that form solutions with water having concentrations no greater than 1 mg/mL, or no greater than 0.1 mg/mL.

Various approaches for improving the solubility properties of drugs have been used. For many substances, solubility can be enhanced by reducing the particle sizes; an increased particle surface area generally results in a more rapid dissolution rate. Sometimes, different polymorphic forms, including crystalline, solvated, and amorphous forms, will have different solubilities and a suitable form can be chosen to meet a specific requirement. However, these approaches are not without difficulties, since very small particles generally have poor flow and handling properties that can affect drug content uniformity, and many polymorphic forms do not have sufficient physical stability to undergo formulation processing and the subsequent storage over a typical product shelf life, without converting to a different form.

The amorphous particles can have increased solubility by overcoming crystal lattice energy. Typically, amorphous drug particles are thermodynamically metastable compared to crystalline states of the substance, but can have significantly enhanced solubility and bioavailability. Solubility can be further classified as equilibrium and supersaturation solubilities. "Equilibrium solubility" is the solubility of the substance in a specific fluid environment, in the absence of a solubilization aid. "Supersaturation" refers to the solubility state of a substance in excess of its equilibrium solubility, characterized by a solubility that is greater than that defined by native solubility of the substance in a given fluid environment. By converting a drug from a crystalline to amorphous form, it is possible to achieve a supersaturation solubility, which in turn can enhance bioavailability. However, significant challenges of chemical and physical drug instability remain. The amorphous state can be viewed as a pseudo-solution state demonstrating greater chemical reactivity, which is reflected in reduced physical and chemical stability and shelf-life. Certain drugs have been commercialized in the amorphous state, where the amorphous form of the drug substance either has acceptable stability over the normal shelf-life of the product, or can be stabilized by other formulation components. In addition, some drugs have been successfully commercialized in a thermodynamically metastable crystalline state.

Amorphous solid dispersion have been used to stabilize amorphous material. A solid dispersion is formed from at least two different components, generally (a) a polymer that can be either crystalline or amorphous and (b) a hydrophobic drug that can be dispersed molecularly, in amorphous particles (clusters) or in crystalline particles. Polymers can improve the physical stability of amorphous drugs in solid dispersions by increasing the glass transition temperature ($T_g$) of the miscible mixture, thus reducing the molecular mobility at usual storage temperatures, or by interacting specifically with functional groups of the drugs. For a polymer to be effective in preventing crystallization, it has to be molecularly miscible with the drug. However, to date, limitations in the development of solid dispersions are predominantly due to physical instability of these systems. Polymeric materials are not in thermodynamic equilibrium below their $T_g$, so the solid polymer approaches its more stable state (lower energy). Also, the effect of moisture on the storage stability of amorphous material is very important as it may increase drug mobility and promote drug crystallization. In addition, many of the polymers used in solid dispersions can absorb moisture, which may result in phase separation, crystal growth or conversion from the amorphous to the crystalline state or from a metastable crystalline form to a more stable structure during storage, all of which may result in decreased solubility and dissolution rate.

For certain patients, swallowing a typical solid pharmaceutical dosage form is difficult. These patients can be elderly, very young, suffering from psychiatric disorders, have oral or esophageal dysfunctions or deformities, etc. When a solid dosage form is preferable, such as to reduce the chances for dosing errors, products have been developed that rapidly disintegrate while being retained in the oral cavity. This disintegration can be a decomposition of the tablet matrix into very small particles and/or dissolution of the matrix in saliva, thereby facilitating swallowing.

An orally disintegrating tablet ("ODT") has been defined by the United States Food and Drug Administration as a solid dosage form containing a medicinal substance that disintegrates rapidly, usually within a matter of seconds, when placed upon the tongue. In general, disintegration is expected to occur within about 30 seconds after the dosage form enters the oral cavity. Such dosage forms are useful for treating pediatric and geriatric patients having difficulties with swallowing tablets, capsules, etc., as well as psychiatric patients having an aversion to the customary swallowed solid forms. The action of saliva is sufficient to achieve the desired result, and mechanical disintegration, such as by chewing, is not required. Desirably, no external liquids will be necessary for swallowing the disintegrated dosage form. An ODT is also sometimes called an "orodispersible" tablet.

The ODT dosage form has certain important requirements, for patient acceptability; these requirements are in addition to the proper disintegration times. Frequently, the taste of the drug substance will be masked, since many substances have bitter or otherwise unpleasant tastes. Also, the mouth feel of the disintegrated tablet is important, so grittiness and the sensation of a residue in the mouth after swallowing should be avoided.

There are several techniques currently in use for making ODT products, including freeze drying or lyophilization of solutions or suspensions, compression of powder blends, molding of melts or pastes, melt granulation, and others. Most of the techniques will prepare tablets that are rather porous to aqueous fluids, thereby promoting rapid disintegration of the matrix in saliva.

An early approach to preparing an orally disintegrating tablet was described in U.S. Pat. No. 4,758,598, where a drug is physically trapped in a freeze-dried matrix composed of a filler (e.g., mannitol) and a polymer (e.g., gelatin). The product is a rather fragile, low-density porous wafer, packaged in the plastic tray where it was formed in a lyophilizer. More recently, U.S. Pat. No. 5,763,476 described an asenapine maleate product prepared in this manner; the drug will be released into saliva and, due to its moderate aqueous solubility, undergoes systemic absorption through the oral mucosa. Other current products are manufactured using this technique.

Although the perception may be that rapid disintegration leads to rapid rates of absorption and bioavailability, this is frequently not observed with poorly soluble drugs. Following dosage form disintegration, it still is necessary for the drug to dissolve before it can be absorbed. It would be advantageous to simultaneously provide rapid disintegration and a drug solubility enhancement in a dosage form.

There is a continuing need for improved pharmaceutical formulations containing low solubility drugs, providing features of oral fast disintegration and higher drug solubility, and therefore faster onset of action for poorly soluble drugs for certain therapeutic classes to improve patient compliance.

SUMMARY OF THE INVENTION

In one aspect of the present invention is an orally disintegrating tablet comprising a dispersion of a poorly water soluble drug and an ionic polymer, wherein said ionic polymer is present in an amount to maintain said poorly water soluble drug in a substantially amorphous form, and wherein said ionic polymer is selected such that said tablet disintegrates within about 30 seconds, and wherein said tablet further comprises at least one additive, excipient, or carrier. In some embodiments, the drug is megestrol or a pharmaceutically acceptable salt thereof.

In one aspect of the present invention is a formulation comprising a solid dispersion or intimate mixture of a poorly water soluble drug and an ionic polymer, wherein said ionic polymer is present in an amount to maintain said poorly water soluble drug in a substantially amorphous form, and wherein said ionic polymer is present in an amount of at least 45% by weight of said formulation. In some embodiments, the ionic polymer is present in an amount of at least about 50% by weight of said formulation. In some embodiments, the ionic polymer is present in an amount of at least about 65% by weight of said formulation. In some embodiments, the ionic polymer is present in an amount ranging from between about 55% to about 75% by weight of said formulation.

In some embodiments, the polymer is an anionic polymer. In some embodiments, the anionic polymer is a copolymer of methacrylic acid and an acrylate selected from the group consisting of ethyl acrylate, methacrylate, and methyl methacrylate.

In some embodiments, the polymer is a cationic polymer. In some embodiments, the cationic polymer is based on a copolymer of dimethylaminoethyl methacrylate, butyl methacrylate, and methyl methacrylate.

In some embodiments, the polymer is a mixture of acetic acid and monosuccinic acid esters of hydroxypropyl methylcellulose.

In some embodiments, the poorly water soluble drug is present in an amount ranging from about 5% to about 75% by weight of said formulation. In some embodiments, the poorly water soluble drug is present in an amount ranging from about 20% to about 50% by weight of said formulation. In some embodiments, the poorly water soluble drug is present in an amount ranging from about 30% to about 50% by weight of said formulation. In some embodiments, the poorly water soluble drug is selected from the group consisting of analgesics, hypnotics, agents for treating bipolar disorder, agents for treating schizophrenia, and agents for treating the central nervous system. In some embodiments, the poorly water soluble drug is selected from the group consisting of megestrol, ziprasidone, eszopiclone, and sumatriptan or pharmaceutically acceptable acids, salts or hydrates thereof.

In some embodiments, the ionic polymer is selected such that said dispersion maintains a glass transition temperature between about 50° C. to about 150° C. In some embodiments, the ionic polymer is selected such that said dispersion maintains a glass transition temperature between about 50° C. to about 120° C. In some embodiments, the composition further comprises at least one additive, excipient or carrier. In some embodiments, the at least one additive, excipient, or carrier is selected from the group consisting of diluents, binders, drug stabilizers, disintegrants, glidants, lubricants, release rate modifiers, anti-oxidants, coatings, colorants, sweeteners, and flavoring agents.

Another aspect of the present invention is an orally disintegrating tablet formulation comprising a dispersion of a poorly water soluble drug and an ionic polymer, wherein said ionic polymer is present in an amount to maintain said poorly water soluble drug in a substantially amorphous form, and wherein said ionic polymer is present in an amount of at least 45% by weight of said formulation and at least one pharmaceutically acceptable additive, excipient, or carrier. In some embodiments, the average particle size of said dispersion ranges from about 100 μm to about 350 μm.

In some embodiments is a method of treating a subject comprising administering a formulation comprising a dispersion of a poorly water soluble drug and an ionic polymer, wherein said ionic polymer is present in an amount to maintain said poorly water soluble drug in a substantially amorphous form, and wherein said ionic polymer is present in an amount of at least 45% by weight of said formulation and at least one pharmaceutically acceptable additive, excipient, or carrier.

In another aspect of the present invention is a formulation comprising megestrol and an ionic polymer, wherein said ionic polymer is present in an amount to maintain said poorly water soluble drug in a substantially amorphous form, and wherein said ionic polymer is present in an amount of at least 65% by weight of said formulation.

In some embodiments of the present invention, the orally disintegrating tablets surprisingly exhibited fast disintegration and enhanced dissolution and bioavailability. In some embodiments, an ionic polymer is selected so as to provide the aforementioned fast disintegration and enhanced dissolution/bioavailability.

In another aspect is a pharmaceutical formulation containing an intimate mixture comprising an amorphous drug having low aqueous solubility and at least one poorly water-soluble ionic polymer. In some embodiments, the intimate mixture is obtained from a molten combination of the drug and polymer. In some embodiments, the intimate mixture is obtained by precipitation from a solution containing the drug and polymer. In some embodiments, the mixture is in the form of an orally disintegrating tablet. In some embodiments, the drug is megestrol or a salt thereof. In some embodiments, the drug is megestrol acetate.

In another aspect, of the present invention is a composition comprising a drug having low aqueous solubility.

In another aspect of the present invention is an orally disintegrating tablet pharmaceutical formulation containing an intimate mixture comprising an amorphous drug having low aqueous solubility and at least one cationic polymer.

In another aspect is an orally disintegrating tablet pharmaceutical formulation containing an intimate mixture comprising an amorphous drug having low aqueous solubility and at least one anionic polymer. In some embodiments, the intimate mixture is obtained from a molten combination of the drug and polymer. In some embodiments, the intimate mixture is obtained by precipitation from a solution containing the drug and polymer. In some embodiments, the polymer is an amino methacrylate copolymer. In some embodiments, the polymer is a methacrylic acid copolymer, Type A. In some embodiments, the polymer is a methacrylic acid copolymer, Type B. In some embodiments, the polymer is a methacrylic acid copolymer, Type C. In some embodiments, the polymer is a hypromellose acetate succinate.

Without wishing to be bound by any particular theory, it has now been discovered that amorphous solid dispersion of poorly soluble drugs prepared with ionic polymers exhibits fast disintegration property when compressed into tablets and therefore is suitable for ODT dosage forms with faster onset of action.

DETAILED DESCRIPTION

Figure 1:
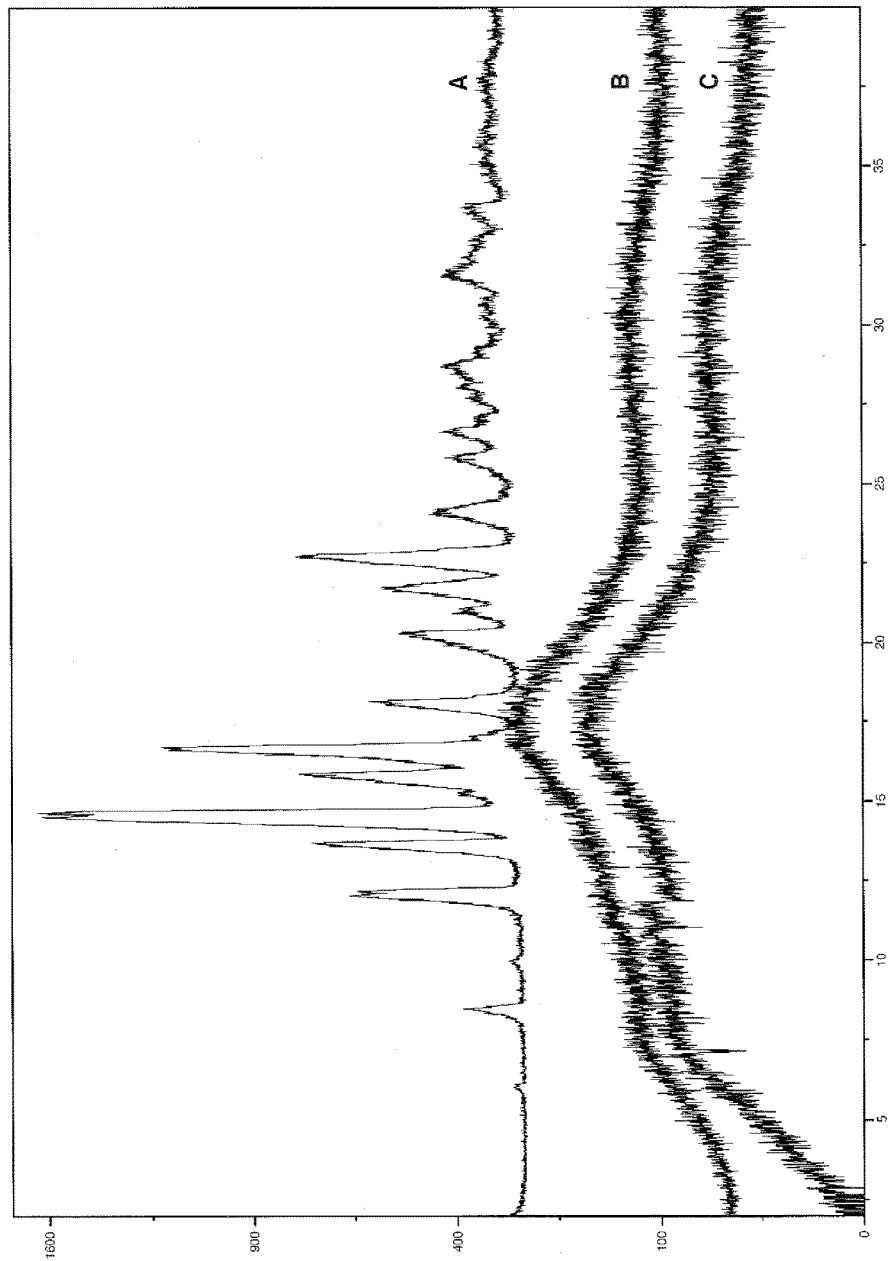
FIG. 1 illustrates comparative X-ray powder diffraction ("XRPD") patterns of initial and stored samples of composition 1A from Example 1.

In some aspects of the present invention is a formulation comprising a dispersion or intimate mixture of a poorly water soluble drug and an ionic polymer. In other aspects of the present invention is a formulation comprising a dispersion or intimate mixture of a poorly water soluble drug and an ionic polymer, wherein said ionic polymer is present in an amount to maintain said poorly water soluble drug in a substantially amorphous form. In yet other aspects of the present invention is a formulation comprising a dispersion or intimate mixture of a poorly water soluble drug and an ionic polymer, wherein said ionic polymer is present in an amount to maintain said poorly water soluble drug in a substantially amorphous form and wherein said ionic polymer is present in an amount of at least 50% by weight of said formulation.

As used herein, the term "substantially" means to meet the criteria in such measure that one skilled in the art would understand that the benefit to be achieved, or the condition or property value desired, is met. In some embodiments, the amount of active agent present in amorphous form is generally in an amount of at least 80% by total weight of the active agent present. In some embodiments, the amount of active agent present in amorphous form is generally in an amount of at least 85% by total weight of the active agent present. In some embodiments, the amount of active agent present in amorphous form is generally in an amount of at least 90% by total weight of the active agent present. In some embodiments, the amount of active agent present in amorphous form is generally in an amount of at least 92.5% by total weight of the active agent present. In some embodiments, the amount of active agent present in amorphous form is generally in an amount of at least 95% by total weight of the active agent present. In some embodiments, the amount of active agent present in amorphous form is generally in an amount of at least 97.5% by total weight of the active agent present. In some embodiments, the amount of active agent present in amorphous form is generally in an amount of at least 99% by total weight of the active agent present.

Aspects of the present disclosure are directed to pharmaceutical formulations of drugs having low solubility in water. Pharmaceutical products can be tested for their drug dissolution characteristics, such as using test 711 "Dissolution" in *United States Pharmacopeia* 24, United States Pharmacopeial Convention, Inc., Rockville, Md., 1999 (the "USP"). Various fluids can be used as the dissolution media, including acids, buffers, simulated digestive tract fluids, etc., and many of these are defined in various monographs of the USP. An example of a procedure uses "Apparatus 2," which has a vessel containing a medium that is stirred with a rotating paddle. Typically, a dosage unit is immersed into the medium and samples of the medium are withdrawn at intervals for drug content analysis, frequently using high performance liquid chromatography ("HPLC") techniques.

The disintegration times of pharmaceutical dosage forms can be determined using the procedure of test 701 "Disintegration" in the USP.

There are various methods currently used for determining the intestinal permeability parameter of drugs, including both in vitro and in vivo techniques. Some of these have been reviewed by D. Volpe, "Application of Method Suitability for Drug Permeability Classification," *The AAPS Journal*, Vol. 12(4), pages 670-678, December 2010.

As used herein, the terms "drugs," "active agents," and "active pharmaceutical ingredients" are used interchangeably.

Suitable drugs for preparing formulations include, but are not limited to, members of the therapeutic categories analgesics, anti-inflammatory agents, anthelmintics, anti-arrhythmic agents, anti-bacterial agents, anti-viral agents, anticoagulants, anti-depressants, anti-diabetic agents, anti-epileptic agents, anti-fungal agents, anti-gout agents, antihypertensive agents, anti-malarial agents, anti-migraine agents, anti-muscarinic agents, anti-neoplastic agents, erectile dysfunction improving agents, immunosuppressants, anti-protozoa agents, anti-thyroid agents, anti-anxiolytic agents, sedatives, hypnotics, neuroleptics, β-blockers, cardiac inotropic agents, corticosteroids, diuretics, anti-Parkinsonian agents, gastrointestinal agents, histamine receptor antagonists, keratolytics, lipid regulating agents, anti-angina agents, cox-2 inhibitors, leucotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, nutritional oils, anti-benign prostate hypertrophy agents, essential fatty acids, non-essential fatty acids, and any combinations of two or more thereof.

Specific examples of suitable active pharmaceutical ingredients include, but are not limited to: abiraterone, acutretin, albendazole, albuterol, aminogluthemide, amiodarone, amlodipine, amphetamine, amphotericin B, atorvastatin, atovaquone, azithromycin, baclofen, beclomethsone, benezepril, benzonatate, betamethasone, bicalutanide, boceprevir, budesonide, bupropion, busulphan, butenafine, calcifediol, calciprotiene, calcitriol, camptothecan, candesartan, capsaicin, carbamezepine, carotenes, celecoxib, cerivistatin, cetrizine, chlorpheniramine, cholecalciferol, cilostazol, cimetidine, cinnarizine, ciprofloxacin, cisapride, clarithromycin, clemastine, clomiphene, clomipramine, clopidrogel, codeine, coenzyme Q10, cyclobenzaprine, cyclosporine, danazol, dantrolene, dexchlopheniramine, diclofenac, dicoumarol, digoxin, dihydroepiandrosterone, dihydroergotamine, dihydrotachysterol, dirithromycin, donepezil, efavirenz, eposartan, ergocalciferol, ergotamine, essential fatty acid sources, eszopiclone, etodolac, etoposide, famotidine, fenofibrate, fentanyl, fexofenadine, finasteride, flucanazole, flurbiprofen, fluvastatin, fosphenytion, frovatriptan, furazolidone, gabapentin, gemfibrozil, glibenclamide, glipizide, glyburide, glymepride, griseofulvin, halofantrine, ibuprofen, irbesartan, irinotecan, isosorbide, isotreinoin, itraconazole, ivermectin, ketoconazole, ketorolac, lamotrigine, lanosprazole, leflunomide, lisinopril, loperamide, loratadine, lovastatin, L-thryroxine, lutein, lycopene, medroxyprogesterone, mefepristone, mefloquine, megesterol, metaxalone, methadone, methoxsalen, metronidazole, metronidazole, miconazole, midazolam, miglitol, minoxidil, mitoxantrone, montelukast, nabumetone, nalbuphine, naratiptan, nelfinavir, nifedipine, nilsolidipine, nilutanide, nitrofurantoin, nizatidine, omeprazole, oprevelkin, osteradiol, oxaprozin, paclitaxel, paricalcitol, paroxetine, pentazocine, pioglitazone, pizofetin, pravastatin, prednisolone, probucol, progesterone, pseudoephedrine, pyridostigmine, rabeprazole, raloxifene, refocoxib, repaglinide, rifabutine, rifapentine, rifaximine, rimexolone, ritanovir, rizatriptan, rosiglitazone, saquinavir, sertraline, sibutramine, sildenafil, simvastatin, sirolimus, spironolactone, sumatriptan, tacrine, tacrolimus, tamoxifen, tamsulosin, targretin, tazarotene, telaprevir, telmisartan, teniposide, terbinafine, terzosin, tetrahydrocannabinol, tiagabine, ticlidopine, tirofibran, tizanidine, topiramate, topotecan, toremifene, tramadol, tretinoin, troglitazone, trovafloxacin, ubidecarenone, valsartan, venlafaxine, vertoporfin, vigabatrin, vitamin A, vitamin D, vitamin E, vitamin K, zafirlukast, zileuton, ziprasidone, zolmitriptan, zolpidem, and zopiclone. This listing is not intended to be exhaustive, as many other drug substances can be used. Also, any of the pharmaceutically acceptable salts, esters, solvates, hydrates and other derivatives that can deliver any of the drugs also can be used, in any polymorphic forms, and combinations of any two or more active ingredients can be used to prepare formulations. Although many of the drugs are commonly formulated using their pharmaceutically acceptable derivatives such as salts and esters, for the sake of brevity only the base drugs have been listed.

Certain classes of drugs, such as analgesics, hypnotics, drugs for treating bipolar disorder and schizophrenia, and other drugs acting on the central nervous system, will desirably have a rapid onset of action to provide more effective therapy. Enhancing the rate of absorption of such drugs is particularly important when they have low solubility, such as those drugs in BCS Classes II and IV. In embodiments, the techniques disclosed herein will increase the rates of drug dissolution in physiologic fluids.

Generally, the amount of drug in the compositions or formulations of the present invention range from about 5% to about 75% of the total weight of the formulation. In some embodiments, the amount of drug in the formulation ranges from about 20% to about 50% by total weight of the formulation. In other embodiments, the amount of drug in the formulation ranges from about 25% to about 40% by total weight of the formulation. In yet further embodiments, the amount of drug in the formulation ranges from about 25% to about 30% by total weight of the formulation.

An aspect of the present disclosure includes intimate mixtures of at least one amorphous drug substance and at least one polymer. The term "intimate mixture" indicates that the components are dispersions where the individual components are not distinguishable using techniques such as optical microscopy, and therefore cannot be simple mixtures of powdered components. In embodiments, the dispersions can be considered solid dispersions, molecular dispersions, or solid solutions of the components.

Suitable polymers for use in forming an intimate mixture include, but are not limited to, ionic polymers, for example: acrylics, such as various products of Evonik Industries, Germany, sold as EUDRAGIT™ copolymers; polyvinyl acetate phthalates; and the more hydrophobic cellulose ether derivatives, such as cellulose acetate phthalates, hypromellose acetate succinates, and hypromellose phthalates (e.g., in HP-50 and HP-55 grades). Typically, the polymers are considered to be poorly water-soluble or even insoluble in water, although they can degrade in fluids having a weakly acidic, neutral, or basic pH, depending on the polymer.

Without wishing to be bound by any particular theory, it is believed that the ionic polymers assist in maintaining the drug or active agent present in a substantially amorphous form, as that term is defined herein. It is also believed, again without wishing to be bound by any particular theory, that the dispersion or intimate mixture of drug and ionic polymer provide for a glass transition temperature between about 50° C. and about 150° C. In other embodiments, the dispersion may maintain a glass transition temperature between about 50° C. and about 100° C. It is also believed that the use of an ionic polymer, versus, for example, a non-ionic polymer, allows for formulations which have a comparatively quicker disintegration time, thus allowing for said compositions to be formulated as orally disintegrating tablets.

The commercial product EUDRAGIT E 100 is a cationic copolymer based on dimethylaminoethyl methacrylate, butyl methacrylate, and methyl methacrylate, having a chemical name "poly(butyl methacrylate-co-(2-dimethylaminoethyl) methacrylate-co-methyl methacrylate) 1:2:1" and categorized in the USP as "amino methacrylate copolymer."

EUDRAGIT L 100-55 is an anionic copolymer based on methacrylic acid and ethyl acrylate, having a chemical name "poly(methacrylic acid-co-ethyl acrylate) 1:1" and categorized in the USP as "methacrylic acid copolymer, Type C."

EUDRAGIT L 100 is an anionic copolymer based on methacrylic acid and methyl methacrylate, having a chemical name "poly(methacrylic acid-co-methyl methacrylate) 1:1" and categorized in the USP as "methacrylic acid copolymer, Type A."

EUDRAGIT S 100 is an anionic copolymer based on methacrylic acid and methyl methacrylate, having a chemical name "poly(methacrylic acid-co-methyl methacrylate) 1:2" and categorized in the USP as "methacrylic acid copolymer, Type B."

Acrylic products are available in various physical forms, for example, EUDRAGIT E PO being a powder form of EUDRAGIT E 100. Polymer products similar to the EUDRAGIT products are commercially available from other sources.

Hypromellose acetate succinate products are available from Shin-Etsu Chemical Co. as AQOAT™ products, as well as from other sources. They are mixtures of acetic acid and monosuccinic acid esters of hydroxypropyl methylcellulose. The USP specification requires that they contain from 12.0 to 28.0 percent of methoxy groups, from 4.0 to 23.0 percent of hydroxypropyl groups, from 2.0 to 16.0 percent of acetyl groups, and from 4.0 to 28.0 percent of succinoyl groups, calculated on the dry basis. For example, the commercially available AQOAT AS-LF product contains 8% acetyl groups and 15% succinoyl groups, the AQOAT AS-MF product contains 9% acetyl groups and 11% succinoyl groups, and the AQOAT AS-HF product contains 12% acetyl groups and 7% succinoyl groups. Ionic polymers have been widely used for enteric or delayed release coating applications, and amorphous solid dispersion stabilization. It has now been discovered that incorporation of ionic polymers using the processes described below can produce orally fast disintegrating tablets (ODT) of poorly soluble dugs with enhanced bioavailbility.

Various methods can be used to prepare intimate mixtures, including combining the drug and polymer and melting the mixture. Another useful method involves treating a solution of the drug and polymer to form a solid mixture, such as by removing the solvent or otherwise precipitating the solid mixture. Solvent may be removed using techniques such as evaporation, for example under a vacuum in a rotary evaporator or thin-film dryer, or by spray drying. Precipitation also can involve combining the solution with an antisolvent or with another reagent that decreases the solubility of the solutes, such as an aqueous acid. These and other solubility-enhancing techniques are discussed below.

Technologies have been, and are continuing to be, developed to improve the dissolution properties of poorly water-soluble drugs, including, but not limited to, the following: salt formation, use of more soluble "prodrug" compounds that form the desired drug due to enzymatic or other chemical reactions within the body, particle size reduction by attrition methods, solubilized formulations, lipid-based formulations, emulsion systems, molecular complexation, co-crystallization, and solid dispersions. Each of these technologies aims to improve oral delivery of poorly-water soluble drugs by increasing dissolution rates and/or enhancing solubility.

Particle size reduction has been repeatedly demonstrated in the pharmaceutical literature to significantly improve the dissolution rates of poorly water-soluble drugs, correspondingly yielding improved absorption and potentially improved drug therapies. Approaches to particle size reduction can be categorized as either "top-down" or "bottom-up" methods. Micronization, wet milling and nano-milling are examples of techniques that can be applied to poorly water-soluble drugs to reduce particle size by top-down approaches. Controlled precipitation, evaporative precipitation into aqueous solution, and micro-precipitation are examples of methods for producing drug particles of reduced size by bottom-up approaches.

In some embodiments, the particles have a size ranging from between about 100 µm to about 350 µm. In other embodiments, the particles have a size ranging from between about 100 µm to about 250 µm.

Solid dispersion technology is a strategy for improving the dissolution properties and hence oral bioavailability of poorly water-soluble drugs. Solid dispersion technology involves dispersing a poorly soluble drug in a solid polymer matrix. The drug can exist in amorphous or crystalline form in the mixture, which provides an increased dissolution rate and/or apparent solubility in gastric and intestinal fluids. Several techniques have been developed to prepare solid dispersions, including co-precipitation, fusion, spray-drying, and hot melt extrusion. Solid dispersion systems provide increased wettable drug particle surface areas that significantly improve dissolution rates. Therefore, the absorption of these compounds can be improved by formulation as a solid dispersion system, if intestinal permeability is not the limiting factor, i.e., BCS Class II compounds.

In hot melt extrusion, a thermoplastic carrier polymer is combined with a drug substance and optionally pharmacologically inert excipients. The mixture is introduced into rotating screws that convey the powder into a heated zone where shear forces are imparted into the mixture, compounding the materials until a molten mass is achieved. Hot-melt extrusion equipment includes an extruder, auxiliary equipment for the extruder, downstream processing equipment, and other monitoring tools used for performance and product quality evaluation. The extruder is typically composed of a feeding hopper, barrels, single or twin screws, and the die and screw-driving unit. The auxiliary equipment for the extruder mainly consists of a heating/cooling device for the barrels, a conveyer belt to cool down the product and a solvent delivery pump. The monitoring devices on the equipment include temperature gauges, a screw-speed controller, an extrusion torque monitor and pressure gauges.

The utilization of differently shaped dies and appropriate downstream processing makes hot-melt extrusion a highly versatile technology for the manufacture of a vast number of different dosage forms. Films can be produced by extruding the material through slit-shaped dies onto cooled rolls which stretch the film to the targeted thickness. Extruded strands may be cut into tablets or pelletized into short cylinders, which can then be spheronized to obtain spherical particles. Cutting may be performed after cooling of the strand on conveyer belts (strand pelletizers), or directly upon extruder exit in the soft state (die-face pelletizers). In addition to cutting operations, monolithic matrices may be obtained by injection molding into tablet-shaped cavities or by calendaring in the soft state between two counter-rotating calendar rolls. Grinding of hot-melt extrudates yields powders which may be directly compressed into tablets or used for dry powder coating applications.

In spray-drying processes, a polymer and drug are first dissolved in an organic solvent and then converted into a powdered solid by atomization of the solution into small droplets and vaporization of the solvent used with heated drying gas. Following solvent evaporation, the dry powder particles are separated from the gas with a filter or cyclone. Due to the large specific surface area offered by the droplets, the solvent rapidly evaporates and the solid dispersion is formed very rapidly, which may be fast enough to prevent phase separation. The solid dispersions prepared by spray drying consist of particles of which the size may be customized by changing the droplet size to meet the requirements for further processing or applications (e.g., free flowing particles or particles for inhalation). Challenges associated with spray-drying processes are related to the fact that both polymer and drug have to be dissolved in an organic solvent to a high solids content that remains sprayable. Also, processing conditions have to be adjusted to avoid thermal stress of the product as well as to yield a product with low level of residual solvents. The advantages of using spray-dried process are related to one step processing from liquid to powder form, quick drying, low thermal stress of the drug, and high throughput rates.

Downstream processing of material prepared by a spray drying process can involve blending of the obtained material with one or more excipients, followed by compression into tablets. A direct-compression process is influenced by the properties of the excipients used such as surface energy and deformation. Further, physico-mechanical properties of properly selected excipients to ensure a robust and successful process include good flowability, good binding functionality, good compressibility, low lubricant sensitivity, and good machineability even in high-speed tableting machinery with reduced dwell times.

A pH-controlled ionic precipitation (PCIP) relies on solvent-controlled precipitation in acidic or basic aqueous solution, therefore it is applicable only for ionic polymers (not for water soluble polymers). PCIP processes include the following: (a) dissolving the drug and ionic polymer in a suitable nonaqueous solvent; and (b) contacting the solution of (a) with an aqueous solution to produce a pH environment in which the ionic polymer is poorly soluble, thereby microprecipitating the therapeutically active compound and ionic polymer as a compound/polymer complex wherein the therapeutically active compound is present in the water-insoluble complex predominantly in amorphous form, as determined by powder X-ray diffraction, and is present in the complex at not less that about 10%, by weight, and the ionic polymer is present in the compound/polymer complex at not less than about 20%, by weight. In some embodiments, the pH of the aqueous solution ranges from about 1 to about 4 for anionic polymers. In other embodiments, the pH of the aqueous solution ranges from about 1 to about 3.5 for anionic polymers. In some embodiments, the pH of the aqueous solution ranges from about 7 to about 11 for cationic polymers. Downstream processing of material prepared by a PCIP method can involve: (a) densification of the obtained material using slugging or roller compaction processes; (b) milling of the material from (a) to produce desired particle sizes; (c) blending of milled material from (b) with one or more suitable excipients; and (d) compression into tablets.

Fluid-bed coating utilizes a fluidized bed coating system, wherein a solution containing a drug and a carrier is sprayed onto particles of excipients, such as sugar or cellulose spheres, to produce either granules ready for tableting or drug-coated pellets for encapsulation in one step. This technique is based on removal of the solvent from the bulk liquid, while the solid precipitates and deposits on the surface of particles simultaneously. The coating process is highly efficient and can be easily scaled up. This method can be applied to both controlled- and immediate-release solid dispersions.

Components of a solid dosage form include, but are not limited to, one or more drug substances, together with any desired number of excipients, such as diluents, binders, drug stabilizers, disintegrants, glidants, lubricants, release rate modifiers, anti-oxidants, coatings, colorants, sweeteners, flavoring agents, etc.

Various useful fillers or diluents according to the present application include, but are not limited to, starches, lactose, cellulose derivatives, confectioner's sugar and the like. Different grades of lactose include, but are not limited to, lactose monohydrate, lactose DT (direct tableting), lactose anhydrous, and others. Different starches include, but are not limited to, maize starch, potato starch, rice starch, wheat starch, pregelatinized starch, and others. Different celluloses that can be used include crystalline celluloses, such as a microcrystalline cellulose, and powdered celluloses. Other useful diluents include, but are not limited to, carmellose, sugar alcohols such as mannitol, sorbitol, and xylitol, calcium carbonate, magnesium carbonate, dibasic calcium phosphate, and tribasic calcium phosphate.

Various useful binders according to the present application include, but are not limited to, hydroxypropyl celluloses in various grades, hydroxypropyl methylcelluloses in various grades, polyvinylpyrrolidones in various grades, copovidones, powdered acacia, gelatin, guar gum, carbomers, methylcelluloses, polymethacrylates, and starches.

Various useful disintegrants include, but are not limited to, carmellose calcium, carboxymethylstarch sodium, croscarmellose sodium, crospovidone (crosslinked homopolymer of N-vinyl-2-pyrrolidone), and low-substituted hydroxypropyl celluloses. Other useful disintegrants include sodium starch glycolate, colloidal silicon dioxide, alginic acid and alginates, acrylic acid derivatives, and various starches.

In embodiments, formulations of the present application can contain at least one antioxidant, for enhancing the stability of a drug. The antioxidant may be present either as a part of a formulation or as a packaging component. Antioxidants can be present in amounts effective to retard decomposition of a drug that is susceptible to oxidation. In embodiments, the content of an antioxidant in the formulations ranges from about 0.001 to 10 weight percent, with respect to the active agent content. Non-limiting examples of antioxidants include one or more of ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate. Other suitable antioxidants will be readily recognized by those skilled in the art.

Useful lubricants include magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

One or more glidant materials, which improve the flow of powder blends, pellets, etc. and help to minimize dosage form weight variations, can be used. Useful glidants include, but are not limited to, silicon dioxide, talc, kaolin, and any combinations thereof.

Sweeteners that can be used include sucrose, sucralose, aspartame, etc.

Useful flavoring agents include pharmaceutically acceptable natural oils, natural flavors, and artificial flavors. Representative flavors include, without limitation thereto, menthol, peppermint, wintergreen, orange, cherry, and other fruits, vanilla, almond and other nuts, etc. Mixtures of two or more flavoring agents frequently are useful.

Coloring agents can be used to color code compositions, for example, to indicate the type and dosage of the therapeutic agent therein. Coloring agents can also be used to differentiate the varied fractions of multi-particulates comprised in a unit dosage form such as a capsule. Suitable coloring agents include, without limitation, one or more natural and/or artificial colorants such as FD&C coloring agents, natural juice concentrates, pigments such as titanium oxide, silicon dioxide, iron oxides, zinc oxide, and the like.

Various solvents that can be used in processes of preparing pharmaceutical formulations of the present disclosure include, but are not limited to, water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N-dimethylformamide, tetrahydrofuran, and any mixtures thereof.

The foregoing lists of excipient substances and processing aids are not intended to be exhaustive, but are merely representative of members of the various categories. Those skilled in the art will be aware of many other useful substances, and their use is specifically contemplated herein. Also, it is well-known that many excipients can serve more than one function in pharmaceutical formulations.

The following examples further describe certain specific aspects and embodiments of the disclosure, and should not be construed as limiting the scope of the disclosure in any manner. In the examples, megestrol acetate is used as a representative for poorly soluble drugs, but it will be apparent to those skilled in the art that the disclosed techniques are also useful for many other drug substances.

EXAMPLE 1

Compositions were prepared using the ingredients and temperatures listed below, where the numbers in parentheses for the ingredients are weight percentages.

| Composition | Ingredients | Temperature |
|---|---|---|
| 1A | Megestrol acetate (40)<br>Methacrylic acid copolymer,<br>Type A* (48)<br>Triethyl citrate (12) | 150-160° C. |
| 1B | Megestrol acetate (40)<br>Methacrylic acid copolymer,<br>Type C** (60) | 140-160° C. |
| 1C | Megestrol acetate (40)<br>Hypromellose acetate<br>succinate*** (60) | 120-140° C. |

-continued

| Composition | Ingredients | Temperature |
|---|---|---|
| 1D | Megestrol acetate (40)<br>Amino methacrylate<br>copolymer**** (60) | 140-150° C. |

*e.g., EUDRAGIT L 100.
**e.g., EUDRAGIT L 100-55.
***e.g., AQOAT AS-LF.
****e.g., EUDRAGIT E PO.

Ingredients were blended in a high-shear mixer and extruded through a 2 mm die using a Leistritz NANO 16 piston-fed twin screw extruder (Leistritz Extrusionstechnik GmbH, Nuremberg, Germany), bottom feed mode, at the indicated temperatures. The extrudate was then milled using a FitzMill Comminutor sold by The Fitzpatrick Company, Elmhurst, Ill. U.S.A. (with screen #1521-0040, medium speed, knife forward) and further characterized as described below.

To evaluate physical stability of the extrudates, as well as efficiency of the proposed process to convert crystalline megestrol acetate to amorphous form, samples of the extrudates were placed in 20 mL amber glass containers and maintained open to the atmosphere for one week at 40° C. and 75% relative humidity ("RH"). The physical form of the drug in the original extrudates and stored samples was determined using X-ray powder diffraction, and results are shown in FIGS. 1 and 2.

Figure 2:
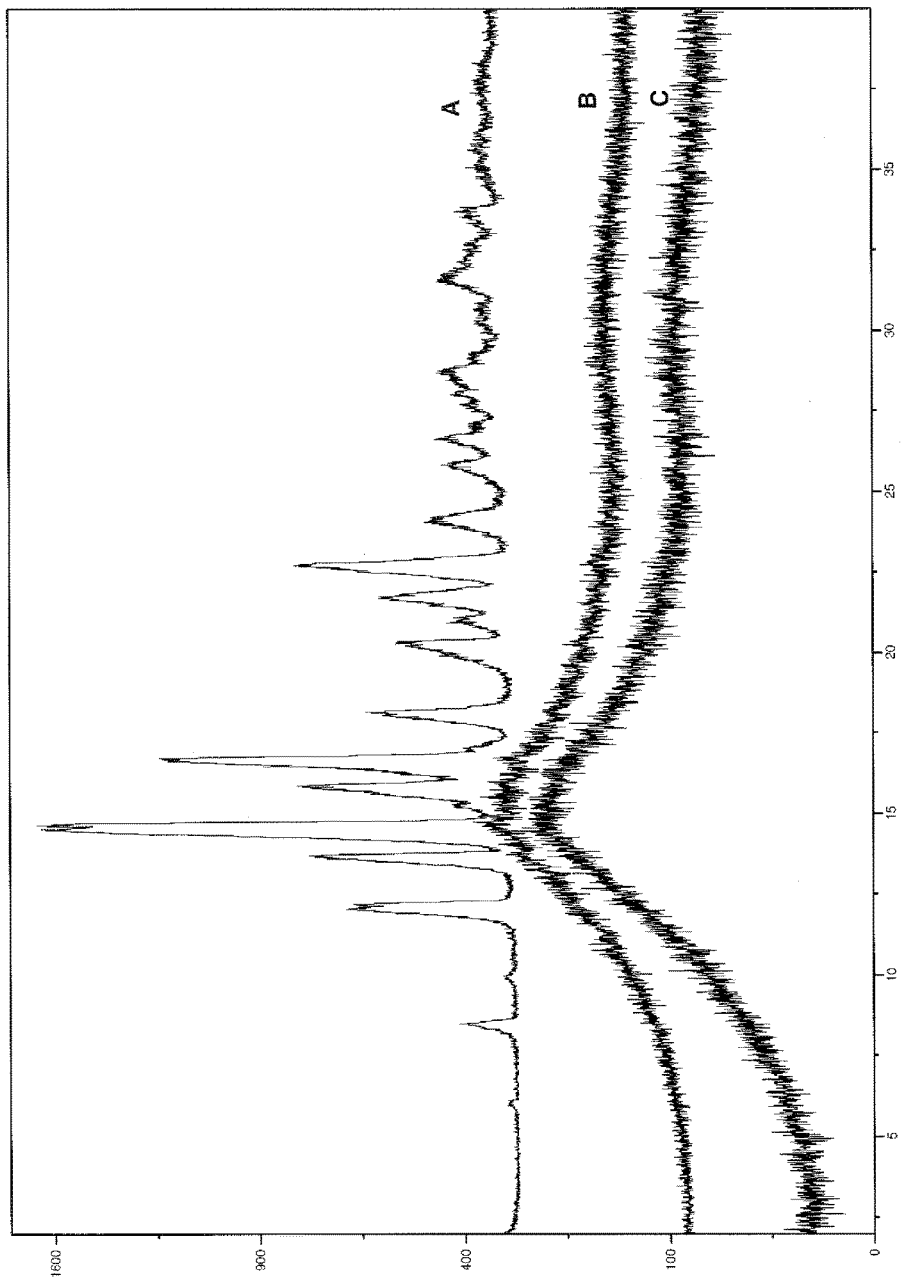
FIG. 2 illustrates comparative XRPD patterns of initial and stored samples of composition 1D from Example 1

In the patterns of FIGS. 1 and 2, the x-axis is in degrees 2θ and the y-axis is intensity units. Curves A and D are patterns for the starting megestrol acetate ingredient. Curve B is for composition 1A, after storage for one week open to the atmosphere at 40° C. and 75% RH. Curve C is for initially prepared composition 1A. Curve E is for composition 1D, after storage for one week, open to the atmosphere at 40° C. and 75% RH. Curve F is for initially prepared composition 1D. All X-ray data presented herein are obtained using copper Kα radiation.

EXAMPLE 2

Compositions were prepared to contain megesterol acetate (40% by weight) and a polymer (60% by weight) using pH-controlled ionic precipitation (PCIP). The drug and an anionic polymer were dissolved in N,N-dimethylacetamide, to form solutions having 20% by weight solute, and cold 0.1N hydrochloric acid is added until a solid precipitates. The solid was separated and washed with 0.1N HCl, then washed twice with cold water and dried overnight at room temperature (25° C.). The resulting powder was then passed through a 40 mesh sieve and packaged for further use.

| Composition | Polymer |
|---|---|
| 2A | Methacrylic acid copolymer,<br>Type A* |
| 2B | Methacrylic acid copolymer,<br>Type C** |
| 2C | Hypromellose acetate<br>succinate*** |

*e.g., EUDRAGIT L 100.
**e.g., EUDRAGIT L 100-55.
***e.g., AQOAT AS-LF.

Figure 3:
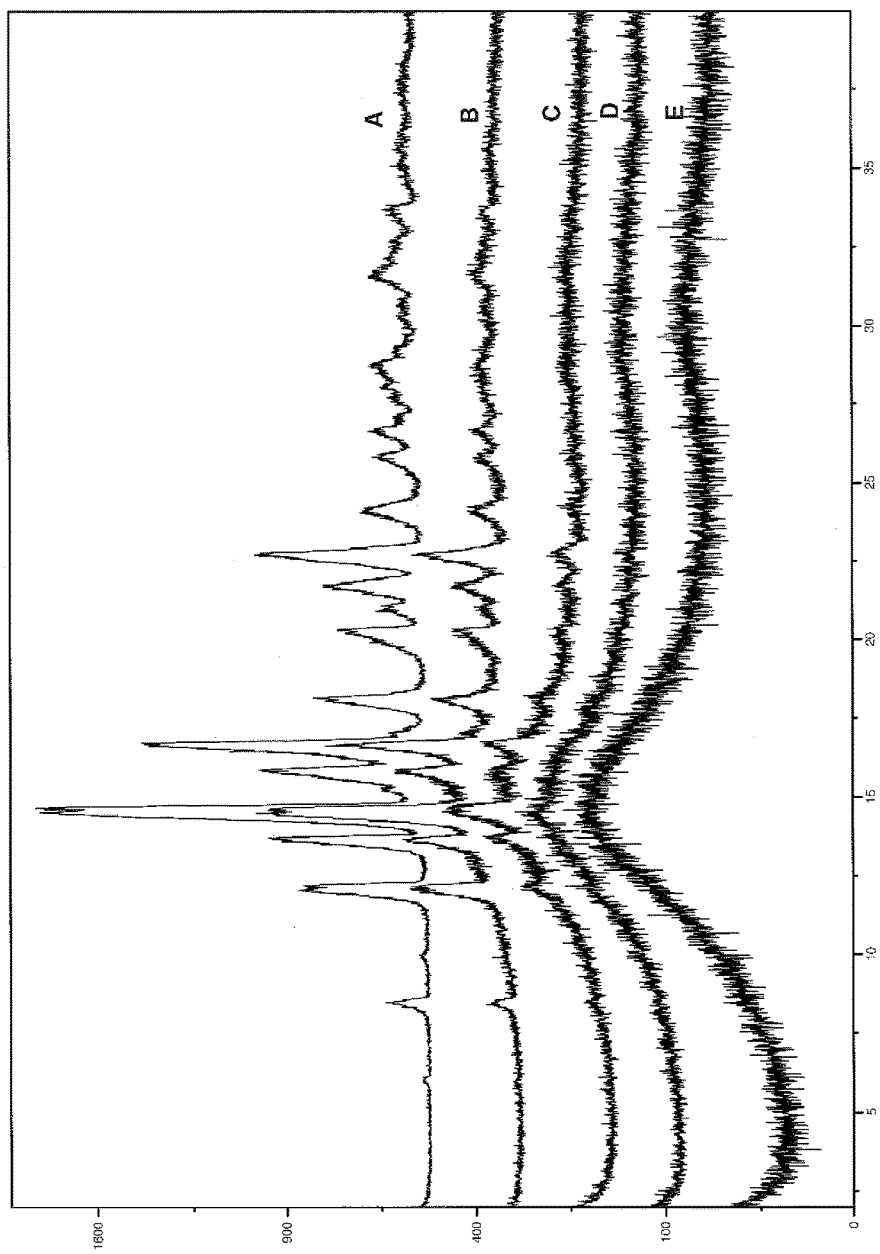
FIG. 3 illustrates comparative XRPD patterns of composition 2E from Example 2, having varying drug to polymer ratios.

FIG. 3 shows X-ray diffraction patterns of the starting megestrol acetate ("A") and samples prepared similarly to composition 2A with the following varying drug to polymer weight ratios: 50:50 ("B"); 40:60 ("C"); 35:65 ("D"); and 30:70 ("E"). X-axis units are degrees 2θ and the y-axis values are intensity units. Without wishing to be bound by any particular theory, it is believed that the crystallinity peaks for this drug disappear when the polymer constitutes at least about 65 percent by weight of the composition, but different drugs can become amorphous using lower or higher amounts of polymer.

EXAMPLE 3

Orally disintegrating tablet formulations 3A-3H were prepared, using the ingredients in the table below.

| Ingredient | mg per Tablet | | | | | | | |
|---|---|---|---|---|---|---|---|---|
| | 3A | 3B | 3C | 3D | 3E | 3F | 3G | 3H |
| Megestrol acetate | 125 | 125 | 125 | 125 | 125 | 125 | 125 | 125 |
| Methacrylic acid copolymer, Type A (EUDRAGIT L 100) | 150 | — | — | — | 150 | — | — | — |
| Amino methacrylate copolymer (EUDRAGIT E PO) | — | 187.5 | — | — | — | 187.5 | — | — |
| Methacrylic acid copolymer, Type C (EUDRAGIT L 100-55) | — | — | 187.5 | — | — | — | 187.5 | — |
| Hypromellose acetate succinate (AQOAT AS-LF) | — | — | — | — | — | — | — | 187.5 |
| Copovidone (KOLLIDON VA64) | — | — | — | 187.5 | — | — | — | — |
| Triethyl citrate | 37.5 | — | — | — | 37.5 | — | — | — |
| Crospovidone | 73 | 73 | 73 | 15 | 15 | 73 | 73 | 15 |
| Mannitol (PARTECK™ 100M) | 130 | 130 | 130 | 45 | 45 | 130 | 130 | 45 |
| Microcrystalline cellulose (VIVAPUR™ 101) | 120 | 120 | 120 | 67.5 | 67.5 | 120 | 120 | 67.5 |
| Sucralose | 2 | 2 | 2 | 4 | 4 | 2 | 2 | 4 |
| Peppermint flavor powder | — | — | — | 4 | 4 | — | — | 4 |
| Magnesium stearate | 4 | 4 | 4 | 2 | 2 | 2 | 4 | 2 |

Procedure:

1. Megestrol acetate and the required members of the next five ingredients listed in the table were blended and extruded in a manner similar to the extrusion of Example 1. The cooled extrudates were passed through a FitzMill™ Comminutor having a 60 mesh screen.
2. Milled extrudates were blended with crospovidone, mannitol, microcrystalline cellulose, sucralose and flavor (if required), then magnesium stearate as added and blended.
3. The blended materials were compressed into tablets, using a force of about 8.9 kN (2000 pounds).

Tablets also were prepared using compositions prepared according to the procedure of Example 2, substituting those compositions for the milled extrudates in step 2, above.

Tablets prepared according to formulations 3A, 3D, 3E, and 3H above were tested for their disintegration times in water, using the USP procedure. Results are shown in the table below.

| Composition | Polymer | Wt. Ratio of Drug to Polymer | Disintegration Time |
|---|---|---|---|
| 3A | EUDRAGIT L 100 | 40:60 | 5 seconds |
| 3D | KOLLIDON VA64 (Non-Ionic Polymer; Comparative Example) | | 25 minutes |
| 3E | EUDRAGIT L100 | | 20 seconds |
| 3H | AQOAT AS-LF | | 22 seconds |

Tablets containing solid dispersions with ionic polymers such as methacrylic acid copolymer, type A (e.g., EUDRAGIT L100) or hypromellose acetate succinate (e.g., AQOAT AS-LF) disintegrate in water rather quickly, i.e., in less than 30 seconds. By optimization of tablet weights and certain excipient components, disintegration times of tablets prepared with ionic polymers can be further improved, to provide disintegration times from 20 seconds to 5 seconds. However, tablets containing solid dispersions prepared with water-soluble nonionic polymers, such as copovidone, disintegrate fairly slowly as demonstrated by the disintegration time of 25 minutes for composition 3D.

Although the present disclosure should not be bound to any particular theory of operation, it is possible that tablets containing an amorphous drug embedded in a poorly water-soluble ionic polymer will quickly disintegrate due to the slow hydration properties of the ionic polymer in water. Solid dispersions prepared with a water-soluble nonionic polymer (e.g., copovidone) might disintegrate more slowly due to rapid hydration properties of the nonionic polymer in water, which hinders its disintegration and consequently retards the drug release.

Figure 4:
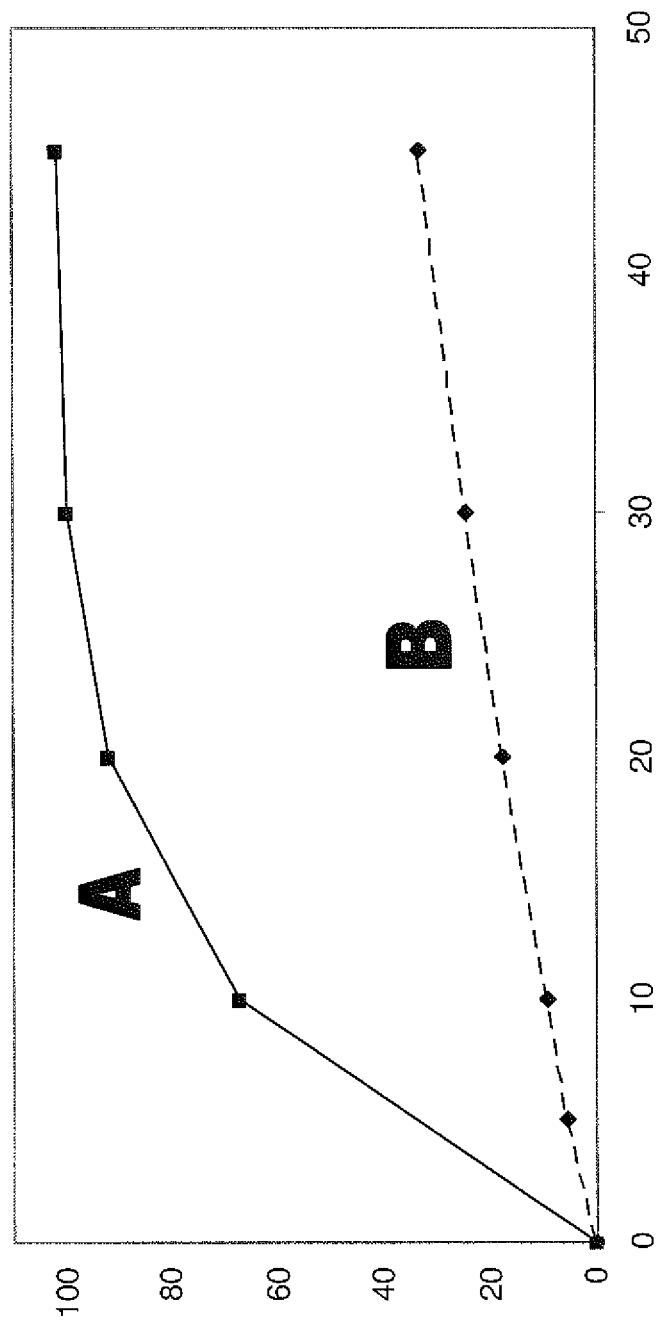
FIG. 4 is a graphical representation of solubility data for compositions from Example 3.

Dissolution testing of compositions 3D and 3H as performed using USP apparatus 2 and 900 mL of 10 mM phosphate buffer (pH 6.8), with 50 rpm rotation. Results are shown in FIG. 4, where the x-axis is minutes and the y-axis is the cumulative percentage of contained drug that dissolves. Curve A is for composition 3H and curve B is for composition 3D. As shown in FIG. 4, the dissolution profile of a composition containing a solid drug dispersion with a poorly water-soluble ionic polymer (composition 3H) exhibits rapid drug release, which could be due to the rapid dosage form disintegration. The composition containing a solid drug dispersion prepared with a water-soluble non-ionic polymer (composition 3D) exhibits slower drug release, which could be due to relatively slower disintegration properties of the dosage form.

Figure 5:
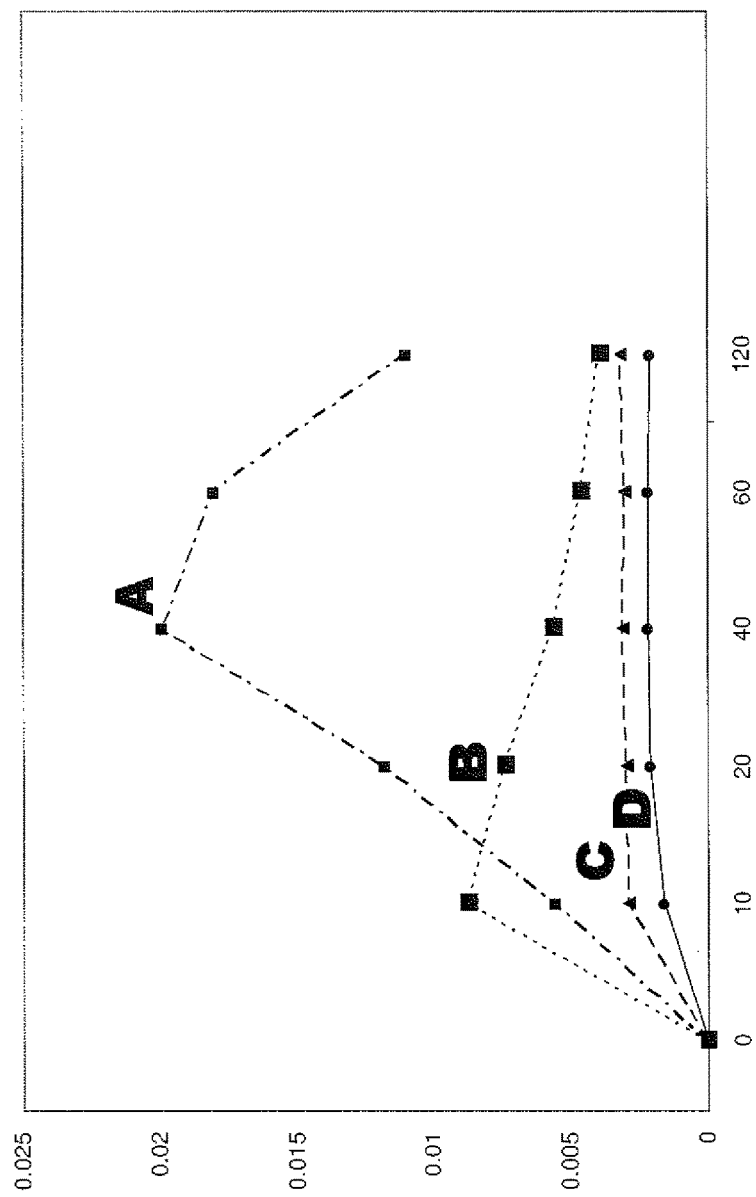
FIG. 5 is a graphical representation of solubility date for ODT compositions.

Solubility testing was conducted, by combining 200 mg of a drug-containing uncompressed final blend composition with 100 mL of 50 mM phosphate buffer (pH 7.5) and placing the mixture in a closed container on a shaker apparatus. Samples (2 mL each) are withdrawn at intervals and analyzed for their dissolved megestrol acetate concentration using ultraviolet spectrophotometry. Results are shown in FIG. 5, where the x-axis is minutes and the y-axis is the drug concentration in mg/mL. Curve A is for composition 3H, curve B is for composition 3A, curve C is for composition 3G, and curve D is for the starting megestrol acetate ingredient.

EXAMPLE 4

Orally disintegrating tablets were prepared, using the procedure described in Example 3 and the ingredients in the following table.

| | mg per Tablet | | | |
|---|---|---|---|---|
| Ingredient | 4A | 4B | 4C | 4D |
| Megestrol acetate | 62.5 | 187.5 | 62.5 | 187.5 |
| Hypromellose acetate succinate (AQOAT AS-LF) | 250 | 125 | — | — |
| Copovidone (KOLLIDON VA64) | — | — | 250 | 125 |
| Crospovidone | 15 | 15 | 15 | 15 |
| Mannitol (PARTECK 100M) | 45 | 45 | 45 | 45 |
| Microcrystalline cellulose (VIVAPUR 101) | 67.5 | 67.5 | 67.5 | 67.5 |
| Sucralose | 4 | 4 | 4 | 4 |
| Peppermint flavor powder | 4 | 4 | 4 | 4 |
| Magnesium stearate | 2 | 2 | 2 | 2 |

The tablets were tested for their disintegration times in water, using the USP procedure, and results are shown below.

| Composition | Polymer | Wt. Ratio of Drug to Polymer | Disintegration Time |
|---|---|---|---|
| 4A | AQOAT AS-LF | 20:80 | 40 seconds |
| 4B | Ionic Polymer | 60:40 | 2 minutes, 36 seconds |
| 4C | KOLLIDON VA64 | 20:80 | 37 minutes, 12 seconds |
| 4D | Non-Ionic Polymer (Comparative Example) | 60:40 | 35 minutes |

As shown in the table, tablets containing solid dispersions with a poorly water-soluble ionic polymer, e.g., hypromellose acetate succinate (AQOAT AS-LF) disintegrate in water significantly faster than tablets containing solid dispersions with a water-soluble nonionic polymer, e.g., copovidone (KOLLIDON VA64).

EXAMPLE 5

Orally disintegrating tablets were prepared, using the procedure described below and the ingredients in the following table.

| | mg per Tablet | | |
|---|---|---|---|
| Ingredient | 5A | 5B | 5C |
| Ziprasidone base | 30 | — | — |
| Eszopiclone | — | 3 | — |
| Sumatriptan Succinate | — | — | 30 |
| Citric acid | 10 | — | — |
| Eudragit EPO | 100 | 10 | 100 |
| Crospovidone | 15 | 10 | 15 |
| Mannitol (PARTECK 100M) | 15 | 40 | 15 |
| Microcrystalline cellulose (VIVAPUR 101) | 15 | 33 | 15 |
| Sucralose | 6 | 2 | 6 |
| Peppermint flavor powder | 2 | 1 | 2 |
| Magnesium stearate | 2 | 1 | 2 |

Procedure:
1. The drug and Eudragit EPO were blended in the PK blender and extruded in a manner similar to the extrusion of Example 1. The cooled extrudates were passed through a FitzMill™ comminutor having a 60 mesh screen.
2. Milled extrudates were blended with crospovidone, mannitol, microcrystalline cellulose, sucralose and flavor, then magnesium stearate is added and blended.
3. The blended materials were compressed into tablets.

The invention claimed is:
1. An orally disintegrating tablet comprising:
   an amorphous solid dispersion comprising a hot-melt extrudate comprising a poorly water soluble drug and an ionic polymer,
   wherein the poorly water soluble drug is selected from the group consisting of: megestrol, ziprasidone, eszopiclone, sumatriptan, and pharmaceutically acceptable salts thereof, and wherein the ionic polymer is selected from the group consisting of:
      a copolymer of methacrylic acid, ethyl acrylate, and methyl methacrylate;
      hypromellose acetate succinate; and
      a copolymer of dimethylaminoethyl methacrylate, butyl methacrylate, and methyl methacrylate; and
   wherein the ionic polymer is present in an amount of at least 45% by weight of the amorphous solid dispersion,
   wherein the poorly water soluble drug and the ionic polymer are present in a drug-to-polymer weight ratio of between 20:80 and 40:60,
   wherein the amount of poorly water soluble drug in amorphous form is present in the amount of at least 80% by weight of the poorly water soluble drug, and
   wherein the tablet disintegrates in water within 40 seconds.
2. The orally disintegrating tablet of claim 1, wherein the poorly water soluble drug is megestrol or a pharmaceutically acceptable salt thereof.

3. The orally disintegrating tablet of claim 1, wherein an amount of the ionic polymer is at least about 55% by weight of said dispersion.

4. The orally disintegrating tablet of claim 1, wherein an amount of the ionic polymer is at least about 65% by weight of said dispersion.

5. The orally disintegrating tablet of claim 1, wherein the poorly water soluble drug is ziprasidone or a pharmaceutically acceptable salt thereof.

6. The orally disintegrating tablet of claim 1, wherein the poorly water soluble drug is eszopiclone or a pharmaceutically acceptable salt thereof.

7. The orally disintegrating tablet of claim 1, wherein the poorly water soluble drug is sumatriptan or a pharmaceutically acceptable salt thereof.

8. The orally disintegrating tablet of claim 1, wherein the poorly water soluble drug and the ionic polymer are present in a drug-to-polymer weight ratio of 20:80, and wherein the tablet disintegrates within 40 seconds.

9. The orally disintegrating tablet of claim 1, wherein the poorly water soluble drug and the ionic polymer are present in a drug-to-polymer weight ratio of 40:60, and wherein the tablet disintegrates within 30 seconds.

\* \* \* \* \*